Dec. 12, 1950 E. G. FISHER Plant Pat. 997
ROSE PLANT
Filed Nov. 22, 1949
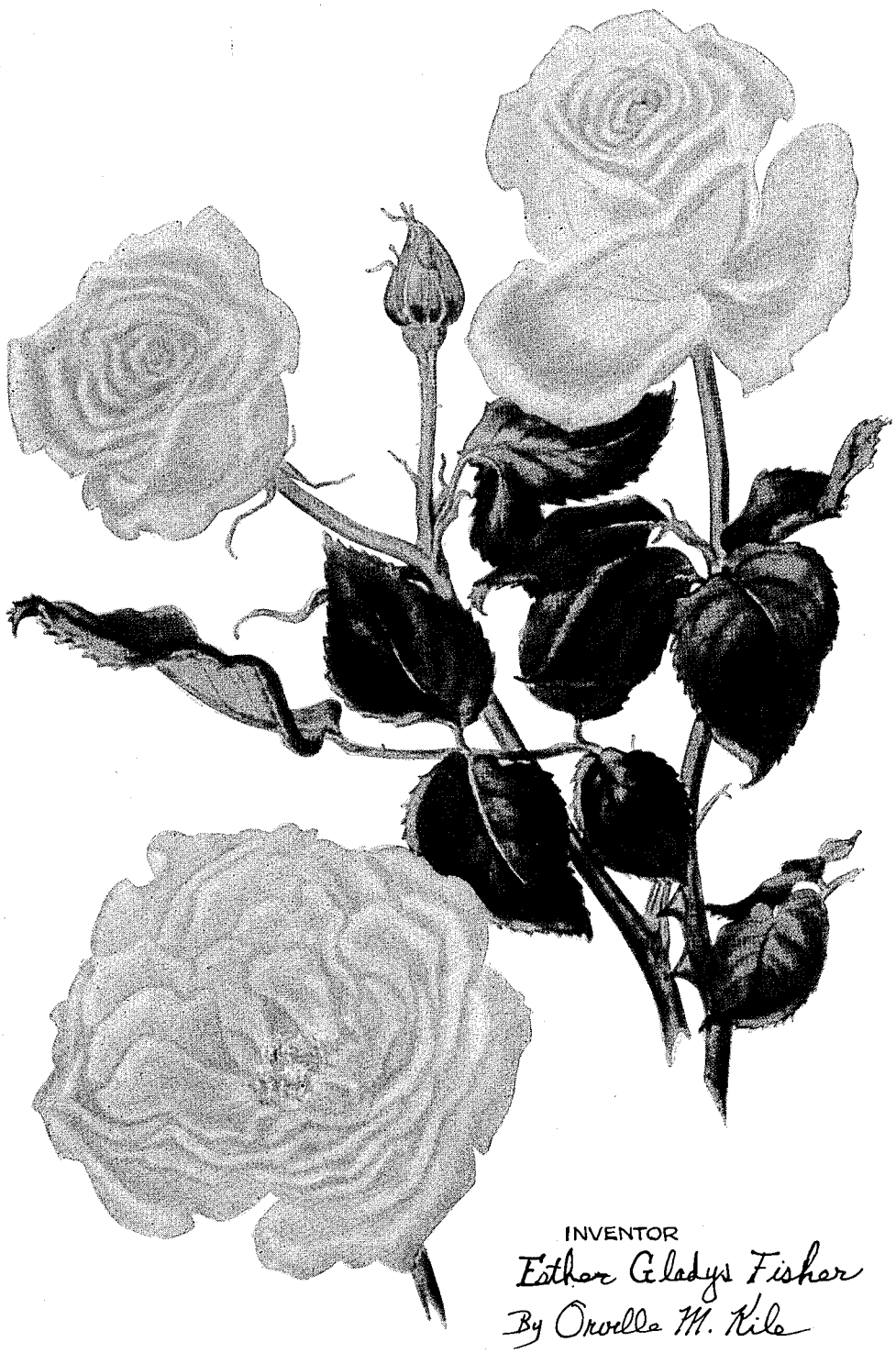
INVENTOR
Esther Gladys Fisher
By Orville M. Kile
PLANT PATENT AGENT Patented Dec. 12, 1950

Plant Pat. 997

UNITED STATES PATENT OFFICE

997

ROSE PLANT

Esther Gladys Fisher, Woburn, Mass., assignor to Arnold-Fisher Company, Woburn, Mass.

Application November 22, 1949, Serial No. 128,746

1 Claim. (Cl. 47—61)

My present invention relates to a new and distinct variety of hybrid tea rose plant particularly adaptable to garden use. It resulted from a cross between the varieties Rome Glory (Plant Patent 304) as the female parent and Better Times (Plant Patent 23) as the male parent, and combines many of the characteristics of its two parents, in addition to some not found in either parent.

The most outstanding feature of the new variety is probably that it is primarily a garden rose, producing many large, beautiful flowers throughout the summer without being forced in a greenhouse. Its vigorous growth resembles that of its female parent, while the coloring of its flower and the new shoots somewhat resembles that of its male parent, although the flower is darker and contains more yellow tinge. The form of the flower is quite different from that of either parent, and it is one of the most fragrant red roses known to me.

The cross which produced this rose variety was made by me in our greenhouse at Woburn, Massachusetts, and in the asexual reproduction by cuttings, also made by me at the same place, its characteristics appear to be permanent.

Illustrations accompanying these specifications show three specimens of the flower of this new variety in various stages of opening, together with portions of the stems and foliage.

Following is a more detailed description of this new rose variety. Color plate numbers refer to Ridgway's Color Standards and Nomenclature and other color names refer to the ordinary dictionary meaning of the term.

*The plant*

Form: Tall bush—about 3½ to 4 feet tall in the field.

Growth: Vigorous and strong.

Blooming habit: Continuous and prolific bloomer as a garden rose.

Hardiness: Much hardier than Better Times, probably about the same as Rome Glory.

Health: Healthy and resistant to most rose diseases.

Stems: Old wood approximately Dark Cress Green (Pl. XXXI), very heavy and long. Thorns rather numerous, sharp, rather small, irregularly placed, slightly downward pointing and usually pink tinted at base. New shoots approximately Pompeian Red (Pl. XIII).

Foliage: Leaflets, 3 to 5.

*Color.*—Dark green, approximately Dark Dull Green (Pl. XXXII) but of shiny appearance, with rachis and under side of leaf frequently tinted with red of approximately Vandyke Red (Pl. XIII) ranging in quantity from very slight shading on the edge to complete coverage of the under side of leaf.

*Texture.*—Substantial and leathery.

*Aspect.*—Glossy on upper surface.

*Size.*—Medium. Terminal leaflet measures up to about 3 inches long by 1¾ inches wide. Lateral leaflets are considerably smaller.

*Shape.*—Elliptical, with acute to acuminate apex and rounded base.

*Edge.*—Simple serrations, sharp but very shallow.

*Rachis.*—Heavy; upper side grooved and usually red-tinged. Under side green, and with several spines.

*The flower*

Bud:

*Size.*—Very small when color first shows. At that time it is approximately 1 inch in length, including ovary. Later it becomes very large before completely expanding.

*Shape.*—Pointed at first. Just before expanding it is somewhat urn-shaped with a slightly depressed and whorled center, the central petals being a little shorter than the outer ones.

*Color.*—Rose Red (Plate XII) or deeper, and tempered with an admixture of yellow.

*Peduncle.*—Very short, bringing the foliage close to the bloom. Smooth except for a few spines. When grown in the open, the peduncle is usually deeply red-tinged.

*Opening.*—Opens slowly and evenly. Not affected by weather conditions.

*Sepals.*—Short, with only slight branching. Reflex early, enfolding the stem tightly.

Bloom:

*Borne.*—Usually borne singly on long stems.

*Form.*—At first globular and full with deep center which is usually in a whorl. Opens with the top almost straight across. Never becomes flat and thin, but becomes cup-shaped, oftentimes with stamens still covered.

*Substance.*—Substantial but not coarse.

*Size of petals.*—The transverse measurement of the outer petals is greater than that from base to tip, averaging 2¾ inches wide by 2½ inches from base to tip. Intermediate petals measure approximately 1¼ inches wide and 1⅞ inches long. Inner petals much narrower.

*Shape of petals.*—Outer petals are broadly obovoid and slightly cupped. Inner petals more nearly spatulate.

*Aspect of petals.*—Slightly velvety.

*Color.*—Upon opening, the bloom is a little darker than the bud, with the outer petals approximately Tyrian Rose (Pl. XII). Later it becomes somewhat darker but does not blue.

*Fragrance.*—Has very intense fragrance which is lasting.

*Petalage.*—Averages 25 petals.

Reproductive organs:

*Pistils.*—Many; tightly bunched; surrounded by pithy ring. *Styles* short and red. *Stigmas* white.

*Stamens.*—Set at outer edge of pithy ring, surrounding pistils; curved inward. Filaments red. Anthers approximately Honey Yellow (Pl. XXX), tinged with red on under side.

*Comparison*

The variety most like my new variety is Better Times but there are many differences, the principal ones as follows:

1. The color of my rose contains much more yellow than that of Better Times.

2. The scent of my rose is much sweeter and more intense.

3. The flower form differs, particularly in that my rose does not have the very small center petals found in Better Times.

4. My variety has much heavier and stronger stems and shoots, and much more vigorous growth.

5. There are more thorns on the stems of my variety.

6. Better Times is excellent in greenhouse but not rated high as a garden rose, while my variety is an excellent garden rose but not so prolific in the greenhouse.

Having thus disclosed my invention, I claim:

The new and improved variety of hybrid tea rose plant, substantially as herein shown and described, characterized particularly by its especial adaptability to garden culture; its strong, tall growth producing heavy canes and shoots; its prolific and constant production of blooms throughout the summer; and the intense fragrance, globular form, excellent keeping quality and deep rose red color of its flowers.

ESTHER GLADYS FISHER.

No references cited.